(12) United States Patent
    Cole et al.

(10) Patent No.: US 12,636,387 B2
(45) Date of Patent: May 26, 2026

(54) SYSTEMS AND METHODS FOR CREATING CUSTOM BRACHYTHERAPY CARRIERS

(71) Applicant: GT MEDICAL TECHNOLOGIES, INC., Tempe, AZ (US)

(72) Inventors: Heidi Cole, Phoenix, AZ (US); David Brachman, Phoenix, AZ (US); John Baker, Gilbert, AZ (US); Adam Turner, Phoenix, AZ (US)

(73) Assignee: GT MEDICAL TECHNOLOGIES, INC., Tempe, AZ (US)

( * ) Notice: Subject to any disclaimer, the term of this patent is extended or adjusted under 35 U.S.C. 154(b) by 1105 days.

(21) Appl. No.: 17/698,348

(22) Filed: Mar. 18, 2022

(65) Prior Publication Data

US 2022/0296922 A1 Sep. 22, 2022

Related U.S. Application Data

(60) Provisional application No. 63/163,366, filed on Mar. 19, 2021, provisional application No. 63/163,583, filed on Mar. 19, 2021.

(51) Int. Cl.
  A61K 51/12 (2006.01)
  A61K 51/08 (2006.01)
  (Continued)

(52) U.S. Cl.
  CPC .......... A61K 51/1262 (2013.01); A61K 51/08 (2013.01); A61N 5/1001 (2013.01);
  (Continued)

(58) Field of Classification Search
  CPC ................ A61K 51/1262; A61K 51/08; A61K 51/1282; A61N 5/1001; A61N 5/1007;
  (Continued)

(56) References Cited

U.S. PATENT DOCUMENTS

D244,393 S    5/1977  Collica et al.
4,427,005 A   1/1984  Tener
  (Continued)

FOREIGN PATENT DOCUMENTS

BR   11 2013 027841 2    4/2012
CA          2835065      2/2018
  (Continued)

OTHER PUBLICATIONS

International Search Report and Written Opinion for International Application No. PCT/US2024/059030 dated Jan. 22, 2025; 10 pages.
  (Continued)

*Primary Examiner* — Carrie R Dorna
*Assistant Examiner* — Joshua Daryl D Lannu
(74) *Attorney, Agent, or Firm* — Knobbe, Martens, Olson & Bear, LLP

(57) ABSTRACT

Custom radioactive seed carriers are fabricated pre-operatively and/or intra-operatively to more precisely match carrier specification of a radiation treatment plan for a particular patient. One or more carrier specification component, such as a 3D printer, injection molding system, machining component, or bioprinter, may be utilized to create the custom carrier.

20 Claims, 9 Drawing Sheets

(51) Int. Cl.

| | |
|---|---|
| *A61N 5/10* | (2006.01) |
| *B29C 33/38* | (2006.01) |
| *B29C 33/40* | (2006.01) |
| *B29C 64/393* | (2017.01) |
| *B29L 31/00* | (2006.01) |
| *B33Y 40/20* | (2020.01) |
| *B33Y 50/00* | (2015.01) |
| *B33Y 80/00* | (2015.01) |
| *B82Y 5/00* | (2011.01) |

(52) U.S. Cl.
CPC ......... *A61N 5/1007* (2013.01); *A61N 5/1014*
(2013.01); *B29C 33/3835* (2013.01); *B29C*
*33/3842* (2013.01); *B29C 64/393* (2017.08);
*B33Y 50/00* (2014.12); *A61N 2005/101*
(2013.01); *A61N 2005/1024* (2013.01); *A61N*
*5/103* (2013.01); *B29L 2031/7546* (2013.01);
*B33Y 80/00* (2014.12)

(58) Field of Classification Search
CPC .................. A61N 5/1014; A61N 5/103; A61N
2005/101; A61N 2005/1024; A61N
5/1027; A61N 2005/1023; A61N 5/1015;
B29C 33/3835; B29C 33/3842; B29C
64/393; B29C 33/40; B33Y 50/00; B33Y
80/00; B33Y 40/20; B29L 2031/7546;
B29L 2031/753; B82Y 5/00
See application file for complete search history.

(56) References Cited

U.S. PATENT DOCUMENTS

| | | | |
|---|---|---|---|
| 4,509,506 A | 4/1985 | Windorski et al. |
| 4,697,575 A | 10/1987 | Horowitz |
| 4,706,652 A | 11/1987 | Horowitz |
| 4,754,745 A | 7/1988 | Horowitz |
| 4,946,435 A | 8/1990 | Suthanthiran et al. |
| 5,030,195 A | 7/1991 | Nardi |
| 5,626,592 A | 5/1997 | Phillips et al. |
| D381,080 S | 7/1997 | Ohata |
| 5,772,574 A | 6/1998 | Nanko |
| 5,803,895 A | 9/1998 | Kronholz et al. |
| 5,840,008 A | 11/1998 | Klein et al. |
| 5,871,708 A | 2/1999 | Park et al. |
| D408,957 S | 4/1999 | Sandor |
| 5,967,966 A | 10/1999 | Kronholz et al. |
| 5,997,842 A | 12/1999 | Chen |
| 6,017,482 A | 1/2000 | Anders et al. |
| D420,452 S | 2/2000 | Cardy |
| D420,745 S | 2/2000 | Cardy |
| D420,746 S | 2/2000 | Cardy |
| 6,066,302 A | 5/2000 | Bray |
| 6,120,533 A | 9/2000 | Fischell |
| 6,129,670 A | 10/2000 | Burdette et al. |
| 6,193,669 B1 | 2/2001 | Degany et al. |
| D443,061 S | 5/2001 | Bergstrom et al. |
| 6,248,057 B1 | 6/2001 | Mavity et al. |
| 6,264,599 B1 | 7/2001 | Slater et al. |
| 6,273,851 B1 | 8/2001 | Slater et al. |
| 6,293,899 B1 | 9/2001 | Sioshansi et al. |
| 6,327,490 B1 | 12/2001 | Spetz |
| 6,352,500 B1 | 3/2002 | Halpern |
| 6,358,195 B1 | 3/2002 | Green et al. |
| 6,360,116 B1 | 3/2002 | Jackson et al. |
| 6,385,477 B1 | 5/2002 | Werner et al. |
| 6,450,937 B1 | 9/2002 | Mercereau et al. |
| 6,458,069 B1 | 10/2002 | Tam et al. |
| 6,468,265 B1 | 10/2002 | Evans et al. |
| 6,471,631 B1 | 10/2002 | Slater et al. |
| 6,512,943 B1 | 1/2003 | Kelcz |
| 6,539,247 B2 | 3/2003 | Spetz |
| 6,547,816 B1 | 4/2003 | O'Foghludha |
| 6,572,526 B1 | 6/2003 | Ford |
| 6,666,811 B1 | 12/2003 | Good |
| 6,679,824 B1 | 1/2004 | Reed et al. |
| 6,699,170 B1 | 3/2004 | Crocker et al. |
| 6,712,508 B2 | 3/2004 | Nilsson et al. |
| 6,712,782 B2 | 3/2004 | Ford |
| D488,864 S | 4/2004 | Fago et al. |
| 6,761,680 B2 | 7/2004 | Terwillieger et al. |
| 6,770,021 B2 | 8/2004 | Halpern |
| 6,787,042 B2 | 9/2004 | Bond et al. |
| 6,790,170 B2 | 9/2004 | Moody et al. |
| 6,846,282 B1 | 1/2005 | Ford |
| 6,971,252 B2 | 12/2005 | Therin et al. |
| 6,994,688 B2 | 2/2006 | Brauckman et al. |
| 7,011,619 B1 | 3/2006 | Lewis |
| 7,070,554 B2 | 7/2006 | White et al. |
| 7,118,729 B1 | 10/2006 | O'Foghludha |
| 7,171,255 B2 | 1/2007 | Holupka et al. |
| 7,190,895 B1 | 3/2007 | Groves et al. |
| D561,896 S | 2/2008 | Jones |
| 7,410,458 B2 | 8/2008 | Bray et al. |
| 7,442,162 B2 | 10/2008 | Henderson et al. |
| D580,056 S | 11/2008 | Orthner |
| D580,057 S | 11/2008 | Ramadani |
| 7,686,756 B2 | 3/2010 | Black et al. |
| 7,736,293 B2 | 6/2010 | Lamoureux et al. |
| 7,749,151 B2 | 7/2010 | Ferguson |
| 7,776,310 B2 | 8/2010 | Kaplan |
| 7,972,261 B2 | 7/2011 | Lamoureux et al. |
| 8,012,455 B2 | 9/2011 | O'Foghludha |
| 8,021,291 B2 | 9/2011 | Lamoureux et al. |
| 8,039,790 B2 | 10/2011 | Cho et al. |
| 8,097,236 B2 | 1/2012 | Aston et al. |
| 8,114,007 B2 | 2/2012 | Lamoureux et al. |
| D657,474 S | 4/2012 | Dona |
| 8,187,159 B2 | 5/2012 | Lamoureux et al. |
| 8,192,345 B2 | 6/2012 | Lamoureux et al. |
| 8,226,539 B2 | 7/2012 | Cutrer |
| 8,293,630 B2 | 10/2012 | Dunkley et al. |
| 8,323,172 B2 | 12/2012 | Black et al. |
| 8,366,598 B2 | 2/2013 | Lamoureux et al. |
| D680,649 S | 4/2013 | Jagger et al. |
| D681,210 S | 4/2013 | Beiriger et al. |
| D681,812 S | 5/2013 | Farris et al. |
| D681,813 S | 5/2013 | Jagger et al. |
| 8,454,489 B2 | 6/2013 | Drobnik et al. |
| D686,341 S | 7/2013 | Nakaji et al. |
| D686,744 S | 7/2013 | Nakaji et al. |
| D686,745 S | 7/2013 | Nakaji et al. |
| D686,746 S | 7/2013 | Nakaji et al. |
| D686,747 S | 7/2013 | Nakaji et al. |
| D686,748 S | 7/2013 | Nakaji et al. |
| D687,568 S | 8/2013 | Nakaji et al. |
| D687,966 S | 8/2013 | Nakaji et al. |
| D687,967 S | 8/2013 | Nakaji et al. |
| 8,600,130 B2 | 12/2013 | Järliden |
| 8,605,966 B2 | 12/2013 | Järliden |
| 8,647,603 B2 | 2/2014 | Aston et al. |
| 8,771,162 B2 | 7/2014 | Lamoureux et al. |
| 8,790,235 B2 | 7/2014 | Lamoureux et al. |
| 8,795,146 B2 | 8/2014 | Lamoureux et al. |
| 8,825,136 B2 | 9/2014 | Giller et al. |
| 8,827,884 B2 | 9/2014 | Ribbing et al. |
| 8,834,837 B2 | 9/2014 | Kelson et al. |
| 8,876,684 B1 | 11/2014 | Nakaji et al. |
| 8,878,464 B2 | 11/2014 | Clayton et al. |
| 8,894,969 B2 | 11/2014 | Kelson et al. |
| 8,915,834 B1 | 12/2014 | Lamoureux et al. |
| 8,939,881 B2 | 1/2015 | Nakaji et al. |
| 8,974,364 B1 | 3/2015 | Nakaji et al. |
| 9,022,914 B2 | 5/2015 | Clayton et al. |
| 9,022,915 B2 | 5/2015 | Nakaji et al. |
| 9,180,310 B2 | 11/2015 | Black et al. |
| 9,358,377 B2 | 6/2016 | Black et al. |
| 9,403,033 B1 | 8/2016 | Brachman |
| 9,409,038 B2 | 8/2016 | Nakaji et al. |
| 9,492,683 B2 | 11/2016 | Brachman et al. |
| 9,526,463 B2 | 12/2016 | Brachman et al. |
| 9,545,525 B2 | 1/2017 | Nakaji et al. |
| 9,642,999 B2 | 5/2017 | Sutton et al. |

(56) References Cited

U.S. PATENT DOCUMENTS

| | | | |
|---|---|---|---|
| 9,788,909 B2 | 10/2017 | Larkin et al. | |
| 9,789,608 B2 | 10/2017 | Itkowitz et al. | |
| 9,808,650 B2 | 11/2017 | White et al. | |
| 9,821,174 B1 | 11/2017 | Fram et al. | |
| 10,058,713 B2 | 8/2018 | Kelson et al. | |
| 10,080,909 B2 | 9/2018 | Brachman et al. | |
| 10,085,699 B2 | 10/2018 | Brachman et al. | |
| 10,265,542 B2 | 4/2019 | Brachman et al. | |
| 10,328,278 B2 | 6/2019 | Krachon et al. | |
| 10,335,613 B2 | 7/2019 | Dikaiou | |
| 10,350,431 B2 | 7/2019 | Nakaji et al. | |
| 10,449,386 B2 | 10/2019 | Bask et al. | |
| 10,646,724 B2 | 5/2020 | Hoedl et al. | |
| 10,888,710 B1 | 1/2021 | Brachman et al. | |
| 10,967,198 B2 | 4/2021 | Herskovic | |
| 10,974,069 B2 | 4/2021 | Maguire et al. | |
| 10,981,018 B2 | 4/2021 | Baker et al. | |
| 11,224,761 B1 | 1/2022 | Wazer et al. | |
| 11,278,736 B2 | 3/2022 | Brachman et al. | |
| 11,298,846 B1 | 4/2022 | Hanberg et al. | |
| 11,413,473 B2 | 8/2022 | Nakaji et al. | |
| 11,673,002 B2 | 6/2023 | Brachman et al. | |
| 12,478,800 B2 | 11/2025 | Nakaji et al. | |
| 2001/0044567 A1 | 11/2001 | Zamora et al. | |
| 2001/0056219 A1 | 12/2001 | Brauckman et al. | |
| 2002/0055666 A1 | 5/2002 | Hunter | |
| 2002/0058853 A1 | 5/2002 | Kaplan | |
| 2002/0058854 A1 | 5/2002 | Reed et al. | |
| 2002/0103410 A1 | 8/2002 | Munro, III et al. | |
| 2002/0120174 A1 | 8/2002 | Steele, Sr. et al. | |
| 2002/0123660 A1 | 9/2002 | Amols'et al. | |
| 2003/0045769 A1 | 3/2003 | Kalas et al. | |
| 2003/0088141 A1 | 5/2003 | Terwilliger et al. | |
| 2003/0088144 A1 | 5/2003 | Terwilliger et al. | |
| 2003/0092958 A1 | 5/2003 | Terwilliger et al. | |
| 2003/0109769 A1 | 6/2003 | Lowery et al. | |
| 2003/0113359 A1 | 6/2003 | Iyer et al. | |
| 2003/0130573 A1 | 7/2003 | Yu et al. | |
| 2003/0149329 A1 | 8/2003 | O'Foghludha | |
| 2003/0153804 A1 | 8/2003 | Tornes et al. | |
| 2003/0208096 A1 | 11/2003 | Tam | |
| 2004/0091421 A1 | 5/2004 | Aston et al. | |
| 2004/0109823 A1 | 6/2004 | Kaplan | |
| 2004/0116767 A1 | 6/2004 | Lebovic et al. | |
| 2004/0225176 A1 | 11/2004 | Flanagan et al. | |
| 2004/0242953 A1 | 12/2004 | Good | |
| 2005/0035310 A1 | 2/2005 | Drobnik et al. | |
| 2005/0111621 A1 | 5/2005 | Riker et al. | |
| 2005/0244045 A1 | 11/2005 | Eriksson | |
| 2005/0267319 A1 | 12/2005 | White et al. | |
| 2006/0015030 A1 | 1/2006 | Poulin et al. | |
| 2006/0058570 A1 | 3/2006 | Rapach et al. | |
| 2006/0063962 A1 | 3/2006 | Drobnik et al. | |
| 2006/0100475 A1 | 5/2006 | White et al. | |
| 2006/0173236 A1 | 8/2006 | White et al. | |
| 2006/0224035 A1 | 10/2006 | Russell, Jr. et al. | |
| 2006/0235365 A1 | 10/2006 | Terwilliger | |
| 2006/0253048 A1 | 11/2006 | Jones | |
| 2007/0021643 A1 | 1/2007 | Lamoureux et al. | |
| 2007/0135673 A1 | 6/2007 | Elliott et al. | |
| 2007/0167665 A1 | 7/2007 | Hermann et al. | |
| 2007/0190761 A1 | 8/2007 | Dunkley et al. | |
| 2007/0225544 A1 | 9/2007 | Vance et al. | |
| 2007/0270627 A1 | 11/2007 | Cutrer et al. | |
| 2008/0004714 A1 | 1/2008 | Lieberman | |
| 2008/0009661 A1 | 1/2008 | Lamoureux et al. | |
| 2008/0058579 A1 | 3/2008 | Hunter et al. | |
| 2008/0058580 A1 | 3/2008 | Black et al. | |
| 2008/0071132 A1 | 3/2008 | Lamoureux et al. | |
| 2008/0146861 A1 | 6/2008 | Murphy et al. | |
| 2008/0207997 A1 | 8/2008 | Higgins et al. | |
| 2008/0221384 A1 | 9/2008 | Chi Sing et al. | |
| 2009/0012347 A1 | 1/2009 | Helle | |
| 2009/0069625 A1 | 3/2009 | Helle et al. | |
| 2009/0131734 A1 | 5/2009 | Neustadter et al. | |
| 2009/0131735 A1 | 5/2009 | Drobnik et al. | |
| 2009/0136422 A1 | 5/2009 | Kelson et al. | |
| 2009/0156880 A1 | 6/2009 | Allan et al. | |
| 2009/0234177 A1 | 9/2009 | Lebovic et al. | |
| 2009/0253950 A1 | 10/2009 | Rapach et al. | |
| 2009/0271715 A1 | 10/2009 | Tumuluri | |
| 2009/0275793 A1 | 11/2009 | Black et al. | |
| 2009/0326314 A1 | 12/2009 | Cutrer et al. | |
| 2010/0015042 A1 | 1/2010 | Keisari et al. | |
| 2010/0056843 A1 | 3/2010 | Fisher et al. | |
| 2010/0056844 A1 | 3/2010 | Fisher et al. | |
| 2010/0056908 A1 | 3/2010 | Giller et al. | |
| 2010/0200778 A1 | 8/2010 | Drobnik et al. | |
| 2010/0210892 A1 | 8/2010 | Lamoureaux et al. | |
| 2010/0228074 A1 | 9/2010 | Drobnik et al. | |
| 2010/0268015 A1 | 10/2010 | Drobnik et al. | |
| 2010/0280374 A1 | 11/2010 | Roberts et al. | |
| 2010/0288916 A1 | 11/2010 | Cho et al. | |
| 2010/0324353 A1 | 12/2010 | Helle | |
| 2011/0013818 A1 | 1/2011 | Eriksson Järliden | |
| 2011/0054235 A1 | 3/2011 | Drobnik et al. | |
| 2011/0206252 A1 | 8/2011 | Eriksson Järliden | |
| 2011/0224494 A1 | 9/2011 | Piskun et al. | |
| 2012/0108882 A1 | 5/2012 | Hoedl | |
| 2012/0165957 A1 | 6/2012 | Everland et al. | |
| 2013/0102832 A1 | 4/2013 | Hoedl et al. | |
| 2013/0102891 A1 | 4/2013 | Binnekamp et al. | |
| 2013/0131434 A1 | 5/2013 | Nakaji et al. | |
| 2013/0209965 A1 | 8/2013 | Fisker | |
| 2013/0338423 A1 | 12/2013 | Nakaji et al. | |
| 2014/0275715 A1* | 9/2014 | Brachman | A61N 5/1007 |
| | | | 600/8 |
| 2014/0296612 A1 | 10/2014 | Schwartz | |
| 2014/0316187 A1 | 10/2014 | Nakaji et al. | |
| 2015/0057487 A1 | 2/2015 | Nakaji et al. | |
| 2015/0105605 A1 | 4/2015 | Finger et al. | |
| 2015/0140535 A1 | 5/2015 | Geri et al. | |
| 2015/0157879 A1 | 6/2015 | Wu et al. | |
| 2015/0196778 A1 | 7/2015 | Nakaji et al. | |
| 2015/0321024 A1 | 11/2015 | Nakaji et al. | |
| 2015/0367144 A1 | 12/2015 | Flynn et al. | |
| 2015/0375012 A1 | 12/2015 | Herskovic | |
| 2016/0242855 A1 | 8/2016 | Fichtinger et al. | |
| 2016/0367709 A1 | 12/2016 | Aston et al. | |
| 2017/0021191 A1 | 1/2017 | Brachman et al. | |
| 2017/0113064 A1 | 4/2017 | Hingston et al. | |
| 2017/0120073 A1 | 5/2017 | Brachman et al. | |
| 2017/0209601 A1 | 7/2017 | Kumar et al. | |
| 2017/0215824 A1 | 8/2017 | Brachman et al. | |
| 2017/0252575 A1 | 9/2017 | Nakaji et al. | |
| 2018/0063386 A1 | 3/2018 | Sharma et al. | |
| 2018/0333509 A1 | 11/2018 | Aston et al. | |
| 2018/0345038 A1 | 12/2018 | Kelson et al. | |
| 2019/0018148 A1 | 1/2019 | Ueno et al. | |
| 2019/0143143 A1 | 5/2019 | Abdalla | |
| 2019/0240504 A1 | 8/2019 | Brachman et al. | |
| 2020/0047001 A1 | 2/2020 | Nakaji et al. | |
| 2020/0086141 A1 | 3/2020 | Finger et al. | |
| 2020/0206372 A1 | 7/2020 | Aston et al. | |
| 2020/0261740 A1 | 8/2020 | Baker et al. | |
| 2020/0261741 A1 | 8/2020 | Herskovic | |
| 2020/0406059 A1 | 12/2020 | Kelson et al. | |
| 2021/0008233 A1 | 1/2021 | Kelson et al. | |
| 2021/0128945 A1 | 5/2021 | Schmidt et al. | |
| 2021/0154340 A1 | 5/2021 | Kelson et al. | |
| 2021/0183492 A1 | 6/2021 | Park | |
| 2021/0236850 A1 | 8/2021 | Baker et al. | |
| 2021/0353960 A1 | 11/2021 | Sienko et al. | |
| 2021/0370083 A1 | 12/2021 | Giladi et al. | |
| 2021/0379096 A1 | 12/2021 | Domankevich et al. | |
| 2022/0096854 A1 | 3/2022 | Carlson | |
| 2022/0184418 A1 | 6/2022 | Arazi et al. | |
| 2022/0212035 A1 | 7/2022 | Kelson et al. | |
| 2022/0296738 A1 | 9/2022 | Brachman et al. | |
| 2022/0347489 A1 | 11/2022 | Brachman et al. | |
| 2023/0012418 A1 | 1/2023 | Nakaji et al. | |
| 2023/0211176 A1 | 7/2023 | Brachman et al. | |
| 2023/0218925 A1 | 7/2023 | Nakaji et al. | |
| 2024/0066318 A1 | 2/2024 | Brachman et al. | |

(56)                References Cited

U.S. PATENT DOCUMENTS

FOREIGN PATENT DOCUMENTS

| | | |
|---|---|---|
| CA | 2834559 | 11/2018 |
| CA | 3017174 | 1/2020 |
| DE | 613 528 | 5/1935 |
| EP | 0 292 630 B1 | 8/1995 |
| EP | 0 906 769 A2 | 4/1999 |
| EP | 1 330 292 | 7/2003 |
| EP | 1 486 230 | 12/2004 |
| EP | 2 968 884 | 1/2016 |
| EP | 2701803 B1 | 8/2018 |
| EP | 3456384 | 3/2019 |
| JP | S52-9424 | 7/1975 |
| JP | H09-028810 | 4/1997 |
| JP | 2001-266903 | 9/2001 |
| JP | 3095304 | 7/2003 |
| JP | 2003-533301 | 11/2003 |
| JP | 2007-512112 | 5/2007 |
| JP | 2009-515603 | 4/2009 |
| JP | 2010-536529 | 12/2010 |
| JP | 6365983 | 7/2018 |
| WO | WO 01/87418 | 11/2001 |
| WO | WO 2007/106531 A1 | 9/2007 |
| WO | WO 2012/100206 A2 | 7/2012 |
| WO | WO 2012/149580 A1 | 11/2012 |
| WO | WO 2012/154988 A2 | 11/2012 |
| WO | WO 2016/171961 | 10/2016 |
| WO | WO 2016/179420 | 11/2016 |
| WO | WO 2017/070147 | 4/2017 |
| WO | WO 2022/198100 A1 | 9/2022 |
| WO | WO 2023/129972 A1 | 7/2023 |
| WO | WO 2023/164585 A1 | 8/2023 |

OTHER PUBLICATIONS

Zhou et al., "Review of advanced catheter technologies in radiation oncology brachytherapy procedures," Cancer Management and Research, 2015: 7, pp. 199-211, Jul. 16, 2015; 13 pages.

Extended European Search Report for Application No. 22772318.6 dated Dec. 3, 2024; 10 pages.

International Search Report and Written Opinion issued in International Application No. PCT/US2022/082483, dated Apr. 26, 2023, in 7 pages.

International Search Report and Written Opinion issued in International Application No. PCT/US2022/021033, dated Jun. 30, 2022, in 7 pages.

International Search Report and Written Opinion issued in International Application No. PCT/US2022/021029, dated Jun. 27, 2022, in 9 pages.

International Search Report and Written Opinion issued in International Application No. PCT/US2023/063174, dated Jun. 15, 2023, in 8 pages.

Cole, P.D., et al., "A comparative long-term assessment of four soft tissue supplements". Anesthetic Surg J. 31(6). 674-681, 2011.

International Search Report; International Application No. PCT/US2012/035907, mailed on Sep. 26, 2012; 3 pages .

International Search Report; International Application No. PCT/US2012/035909, mailed on Aug. 30, 2012; 3 pages.

Crepeau, R.H., et al., "Image Processing of Imperfect Protein Arrays: Sectioned Crystals and Tubulin Sheets and Rings". Elec. Microsc. Soc. Amer. Proc. 40:84-87, 1982.

Crepeau, R.H., et al., "Reconstruction of imperfectly ordered zinc-induced tubulin sheets using cross- correlation and real space averaging". Ultramicroscopy, 6, 7-18, 1981.

Dagnew, E., et al., "Management of newly diagnosed single brain metastasis using resection and permanent iodine-125 seeds without initial whole-brain radiotherapy: a two institution experience". Neurosurg Focus. 15; 22(3):E3, 2007.

Delaney, T.F., et al., "Intraoperative dural irradiation by customized 192 iridium and 90 Yttrium brachytherapy plaques". Int. J. Radiat Oncol Biol Phys. 57(1): 239-245, 2003.

Ewersten, et al., "Biopsy Guided by Real-Time Sonography Fused with MRI: A Phantom Study", American Journal of Roentgenology. 2008; 190: 1672-1674. 10.2214/AJR.07.2587.

Gutin, P.H., et al., "A coaxial catheter system for after loading radioactive sources for the interstitial irradiation of brain tumors. Technical note". J. Neurosurg 56: 734-735, 1982.

Gutin, P.H., et al., "Brachytherapy of recurrent tumors of the skull base and spine with iodine-125 sources". Neurosurgery 20:938-945, 1987.

Hamilton, A.J., et al., "The use of gold foil wrapping for radiation protection of the spinal cord for recurrent tumor therapy". Int. J. Radiat Oncol Biol Phys. 32(2):507-511, 1995.

Hilaris, B.S., et al., "Interstitial irradiation for unresectable carcinoma of the lung". Ann Thoracic Surg; 20:491-500, 1975.

Hilaris, B.S., et al., "Intraoperative radiotherapy in stage I and II lung cancer". Semin Surg Oncol. 3:22-32, 1987.

Huang, K., et al., "Surgical resection and permanent iodine-125 brachytherapy for brain metastases". J. Neurooncol. 91:83-93, 2009.

Jenkins, H.P., et al., "Clinical and experimental observations on the use of a gelatin sponge or foam". Surg 20:124-132, 1946.

Kneschaurek, P. et al.: "Die Flabmethode Zur Intraoperativen Bestrahlung. Öthe Flab-Method for Intraoperative Radiation Therapy", Strahlentherapie und Oknologie, Urban Und Vogel, Muenchen, DE, vol. 171, No. 2; Feb. 1, 1995, pp. 61-69, XP000610565, ISSN:0179-7158.

Marchese, M.J., et al., "A versatile permanent planar implant technique utilizing iodine-125 seeds imbedded in gelfoam". Int J Radiat Oncol Biol Phys 10:747-751, 1984.

Miller, S., et al., "Advances in the virtual reality interstitial brachytherapy system." Engineering Solutions for the Next Millenium. 1999 IEEE Canadian Conference on Electrical and Computer Engineering (Cat. No. 99TH8411). vol. 1. IEEE, 1999.

Murphy, M.K., et al., "Evaluation of the new cesium-131 seed for use in low-energy x-ray brachytherapy". Med Phy 31(6): 1529-1538, Jun. 2004.

Nori, D., et al., "Intraoperative brachytherapy using Gelfoam radioactive plaque implants for resected stage III non-small-cell lung cancer with positive margin: A pilot study". J Surg Oncol. 60:257-261, 1995.

Parashar, B., et al., "Cesium-131 permanent seed brachytherapy: Dosimetric evaluation and radiation exposure to surgeons, radiation oncologists, and staff". Brachytherapy. 10:508-511, 2011.

Patel, S., et al., "Permanent iodine-125 interstitial implants for the treatment of recurrent Glioblastoma Multiforme". Neurosurgery 46 (5) 1123-1128, 2000.

Rivard, M.J., "Brachytherapy dosimetry parameters calculated for a 131 Cs source". Med Phys. 34(2): 754-765, 2007.

Rogers, C.L., et al., "Surgery and permanent 125-1 seed paraspinal brachytherapy for malignant tumors with spinal cord compression". Int. J. Radial Oncol Biol Phys. 54(2): 505-513, 2002.

Wernicke, A.G., et al., "Feasibility and safety of Gliasite brachytherapy in the treatment of CNS tumors following neurosurgical resection". J. Cancer Res Ther. 6(1), 65-74, Jan.-Mar. 2010.

CivaSheet; "Precision Therapy Without The Beam"; CivaTech Oncology Inc.; CivaTech; https://civatechoncology.com/professionals/civasheet/2 pages; Accessed on Oct. 2018.

CivaSheet; "Precision Therapy Without The Beam"; CivaTech Oncology Inc.; CivaTech; https://civatechoncology.com/products-2/products/; 5 pages; Accessed on Oct. 2018.

Aima, Manik et al.; "Dosimetric Characterization of a New Directional Low-Dose Rate Brachytherapy Source"; Department of Medical Physics; Mar. 11, 2018; 32 pages.

Rivard, Mark J.; "A Directional Pd Brachytherapy Device: Dosimetric Characterization and Practical Aspects for Clinical Use"; Department of Radiation Oncology; Brachytherapy 16 (2017) pp. 421-432.

Office Action dated Apr. 2, 2015; European Patent Application No. 12724426.7; 5 pages.

Office Action dated Oct. 30, 2015; European Patent Application No. 12724426.7; 4 pages.

Office Action dated Feb. 9, 2016; Japanese Application No. 2014-508190; 7 pages including english translation.

(56)         References Cited

OTHER PUBLICATIONS

International Search Report; International Application No. PCT/US2016/031035; filed May 5, 2016; 15 pages; mailed on Aug. 5, 2016.
International Search Report and Written Opinion; International Application No. PCT/US2016/027143, filed Apr. 12, 2016; mailed on Aug. 25, 2016; 7 pages.
Decision of Rejection dated Feb. 4, 2016, Japanese Patent Application No. 2014-508190 with English Translation; 4 pages.
Search and Examination Report; Application No. P1140/13; Filed on Oct. 24, 2013 (PCT Apr. 30, 2012); 10 pages.
Summons to Attend Oral Proceedings dated Aug. 18, 2017; European Application No. 12724426.7; 5 pages.
Office Action dated Nov. 2, 2017; European Patent Application No. 12724427.5; 4 pages.
Extended European Search Report; Application No. 18186392.9; dated Jan. 7, 2019; 7 pages.
Extended European Search Report for Application No. 23760942.5 dated Oct. 27, 2025; 10 pages.
Extended European Search Report for Application No. 22917538.5 dated Nov. 11, 2025; 11 pages.

\* cited by examiner

Pre-Operative Process

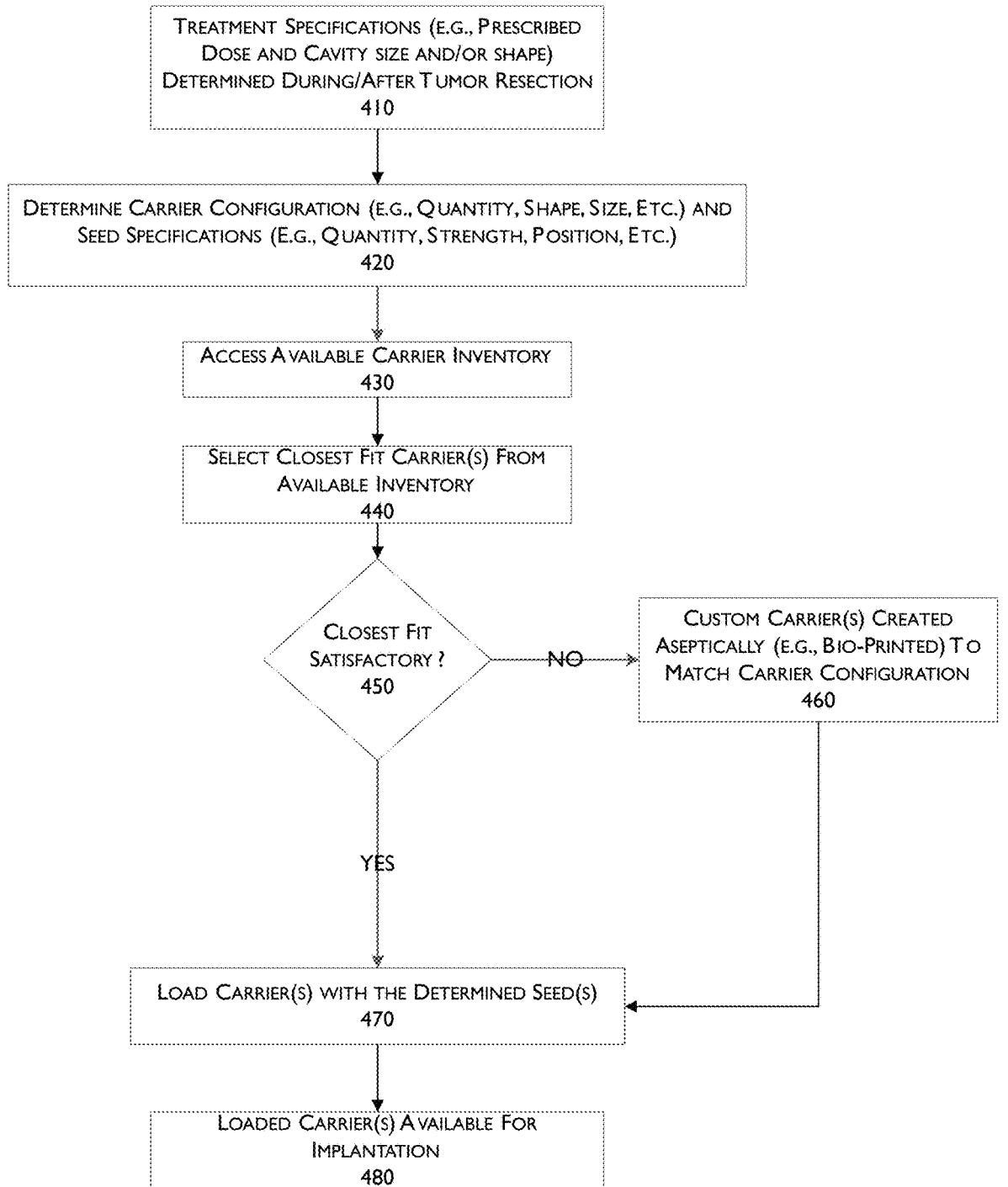

Intra-Operative Process

TREATMENT SPECIFICATIONS (E.G., PRESCRIBED
DOSE AND CAVITY SIZE AND/OR SHAPE)
DETERMINED DURING/AFTER TUMOR RESECTION
410

DETERMINE CARRIER CONFIGURATION (E.G., QUANTITY, SHAPE, SIZE, ETC.) AND
SEED SPECIFICATIONS (E.G., QUANTITY, STRENGTH, POSITION, ETC.)
420

ACCESS AVAILABLE CARRIER INVENTORY
430

SELECT CLOSEST FIT CARRIER(S) FROM
AVAILABLE INVENTORY
440

CLOSEST FIT
SATISFACTORY ?
450

NO

CUSTOM CARRIER(S) CREATED
ASEPTICALLY (E.G., BIO-PRINTED) TO
MATCH CARRIER CONFIGURATION
460

YES

LOAD CARRIER(S) WITH THE DETERMINED SEED(S)
470

LOADED CARRIER(S) AVAILABLE FOR
IMPLANTATION
480

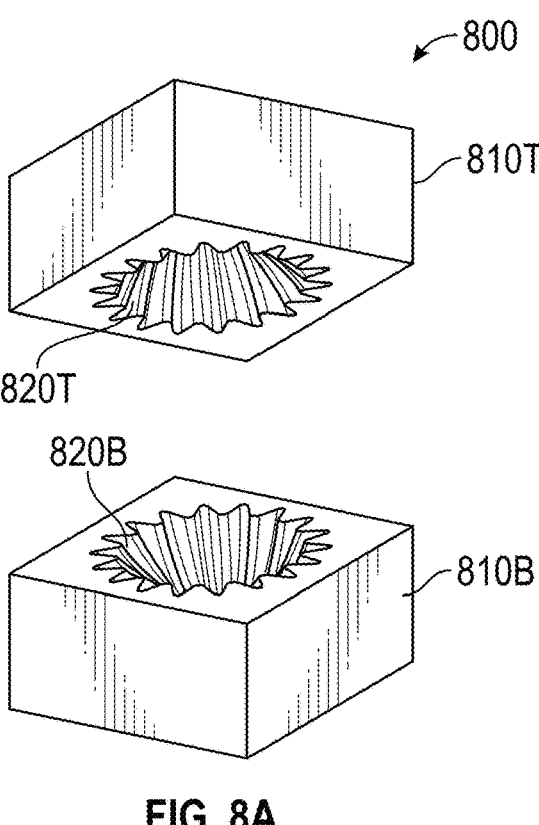
FIG. 8A
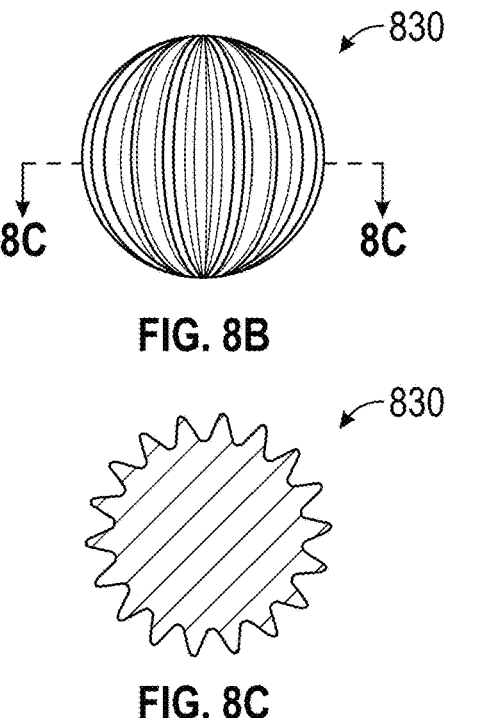
FIG. 8B
FIG. 8C

900

SYSTEMS AND METHODS FOR CREATING CUSTOM BRACHYTHERAPY CARRIERS

FIELD

The invention generally relates to improvements to customization of radioactive seed carriers for use in brachytherapy.

BACKGROUND

Tumors in living organisms are highly variable in size, location and their amount of infiltration into normal tissues, and the variability of tumors in general make them very difficult to treat with a one-size fits all approach. Furthermore, the extent of tumors and/or void created upon debulking are typically not known until presented in the operating room. Thus, the options necessary to effectively treat a tumor or tumor bed need to be quite diverse.

Brachytherapy involves placing a radiation source either into or immediately adjacent to a tumor. It provides an effective treatment of cancers of many body sites. Brachytherapy, as a component of multimodality cancer care, provides cost-effective treatment. Brachytherapy may be intracavitary, such as when treating gynecologic malignancies; intraluminal, such as when treating esophageal or lung cancers; external surface, such as when treating cancers of the skin, or interstitial, such as when treating various central nervous system tumors as well as extracranial tumors of the head and neck, breast, lung, soft tissue, gynecologic sites, liver, prostate, and skin.

SUMMARY

The systems, methods, and devices described herein each have several aspects, no single one of which is solely responsible for its desirable attributes. Without limiting the scope of this disclosure, several non-limiting features will now be described briefly.

Discussed herein are methods and apparatuses for manufacturing custom radioactive seed carriers for providing adjuvant radiation therapy around a tumor cavity of a patient. The custom carriers may be created using a 3D printer that is programmed to generate a mold for the custom carrier based on carrier specifications of a patient treatment plan. The mold may then filled with collagen (e.g., human-derived or bovine-derived) and/or another bioresorbable material to create a custom carrier. One or more radioactive seeds may then be embedded in the carrier, the carrier may be lyophilized (e.g., freeze dried), sterilized, and shipped to a surgical center where the carrier is ready for placement in the tumor cavity. In some embodiments, injection molding may be used to create a custom mold for creating a custom radioactive carrier. In some embodiments, a bioprinter may be used to print a custom carrier, such as by printing layers of collagen that are customized based on a patient treatment plan. These and other embodiments are discussed in further detail herein.

BRIEF DESCRIPTION OF THE DRAWINGS

The principles of the present invention will be apparent with reference to the following drawings, in which like reference numerals denote like components:

FIG. 4 is a flowchart illustrating one embodiment of an intra-operative process for generating custom loaded carriers.

FIG. 8A is a perspective view of another custom mold that is configured to produce a spherical fluted carrier.

FIG. 8B is a side view of the custom carrier created with the mold of FIG. 8A.

FIG. 8C is a sectional view of the cross-section of the custom carrier indicated in FIG. 8B.

DETAILED DESCRIPTION

Figure 1:
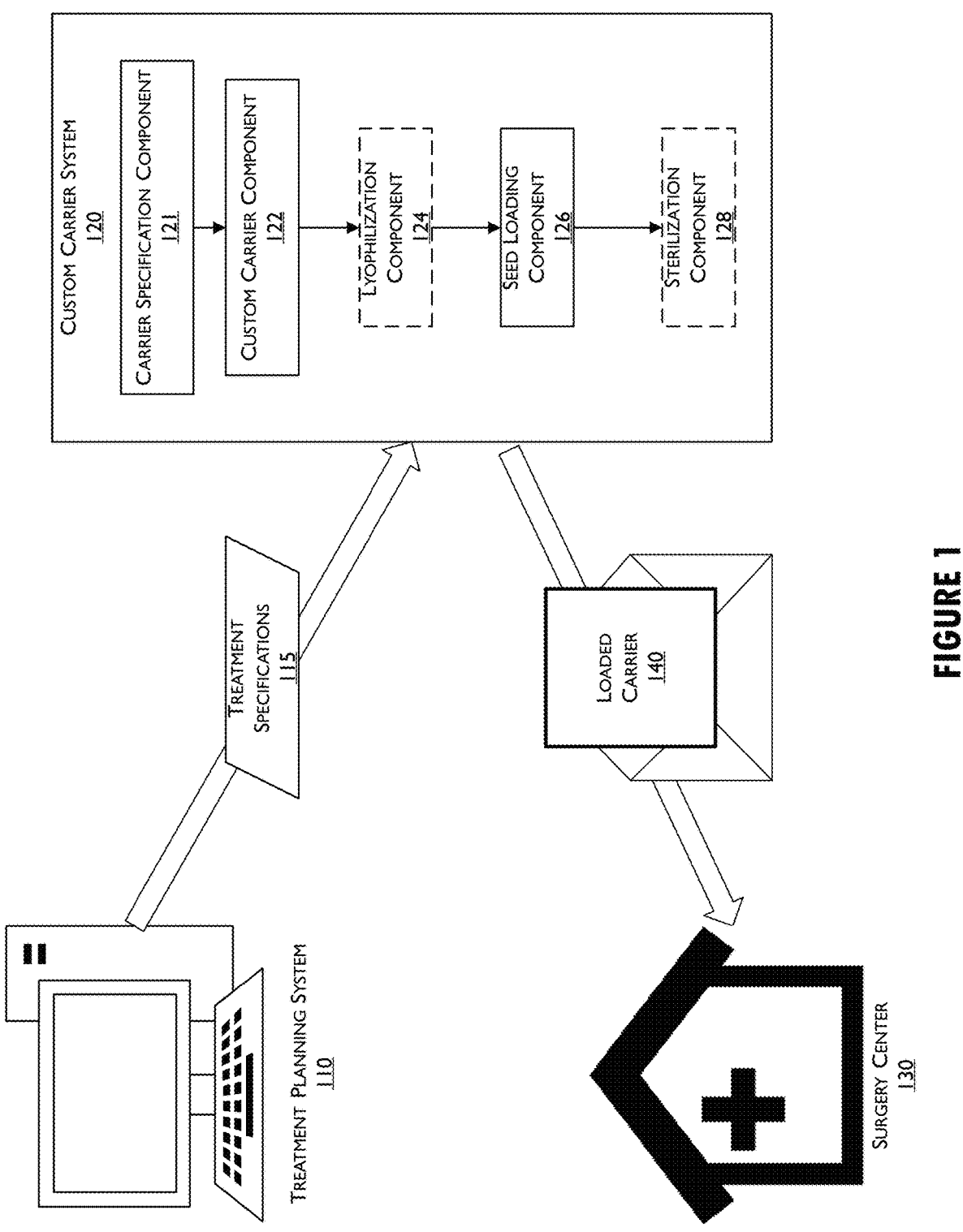
FIG. 1 is a high-level diagram of a system of devices usable to create custom carriers for use in brachytherapy.

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Illustrative embodiments are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another.

Terms

To facilitate an understanding of the systems and methods discussed herein, several terms are described below. These terms, as well as other terms used herein, should be construed to include the provided descriptions, the ordinary and customary meanings of the terms, and/or any other implied meaning for the respective terms, wherein such construction is consistent with context of the term. Thus, the descriptions below do not limit the meaning of these terms, but only provide example descriptions.

Tumor: an abnormal growth of tissue resulting from uncontrolled, progressive multiplication of cells. Tumors can be benign or malignant.

Tumor bed: an anatomical area of a patient (e.g., a human or other mammal) where a tumor exists (pre-operative tumor bed) and/or an area surrounding a surgically removed tumor (post-operative tumor bed), such as a cranial cavity from which a tumor was surgically removed. Even after surgical removal of a tumor, the remaining tumor bed of the patient may include tumor cells.

Treatment area: an anatomical area that is targeted for delivery of radiation, such as from one or more radiation delivery devices (e.g., the carriers discussed below). A treatment area may include tissue below and/or around a location where the radiation deliver device is positioned, such as an anatomical area of a tumor or a tumor bed.

Treatment surface: an anatomical surface of a patient (e.g., a human or other mammal) where a radiation delivery device is to be placed to deliver radiation to a treatment area, such as the treatment surface itself and/or tissue below the treatment surface. A treatment surface may be a portion of a tumor bed or any other anatomical surface. For example, if a tumor bed is surgically created, the treatment surface may include an entire exposed surface of the tumor bed, a portion of such exposed surface, or the entire exposed surface of the tumor bed as well as a surrounding area of tissue.

Brachytherapy: radiation treatment in which the radiation delivery device is placed directly on and/or close to a treatment surface of the body, such as directly on the surface of the body, within the body, or in a tumor bed. For example, brachytherapy may be intracavitary, such as in cranial or gynecologic malignancies; intraluminal, such as in esophageal or lung cancers; external, such as in cancers of the skin; and/or interstitial, such as in treatment of various central nervous system tumors as well as extracranial tumors of the head, neck, lung, soft tissue, gynecologic sites, rectum, liver, prostate, and penis.

Seed: a radioactive material that is configured for delivery of radiation to a tumor and/or tumor bed. A seed may be in various shapes and sizes, such as cylinder, cone, sphere, pyramid, cube, prism, rectangular prism, triangular prism, and/or any combination of these or other shapes. While seeds are generally referred to herein as cylindrical, any other shape or size of seed may alternatively be used in the various systems and methods discussed herein. Seeds may comprise any combination of one or more of multiple radioactive components, such as Cs 131, Ir 192, I 125, Pd 103, for example. Seeds may include a protective outer shell that partially or fully encases the radioactive material. Seeds are one form of radiation source. The term "radiation source," as used herein, generally refers to a radioactive seed (or other object that emits radiation), either alone (e.g., a seed) or embedded, or otherwise attached to, a carrier (e.g., a tile carrier with an embedded radioactive seed).

Carrier: a substrate that holds or contains a radioactive seed. A carrier that contains one or more seeds is a radiation delivery device. Carriers may comprise various materials, such as one or more bioresorbable materials, such as collagen. Thus, these bioresorbable materials are biodegradable, or naturally absorbing into the mammalian tissue over time, such as over a period of weeks or months. Carriers may be configured for permanent implantation into a tumor bed, such as to provide radioactive energy to a treatment surface surrounding an area where a tumor has been removed in order to treat any remaining malignant tissue. Carriers can be composed of various materials and take on various shapes and sizes. Examples carriers, such as carriers having various sizes, shapes, configurations, etc., are included in the following patent and patent application, each of which is hereby incorporated by reference in its entirety and for all purposes:

U.S. patent application Ser. No. 14/322,785, filed Jul. 2, 2014, now U.S. Pat. No. 8,876,684, entitled "Dosimetrically Customizable Brachytherapy Carriers and Methods Thereof In The Treatment Of Tumors," and U.S. patent application Ser. No. 14/216,723, filed Mar. 17, 2014, now U.S. Pat. No. 9,492,683, entitled "Dosimetrically Customizable Brachytherapy Carriers and Methods Thereof In The Treatment Of Tumors."

U.S. Patent Application No. 63/163,583, filed Mar. 19, 2021, entitled "Custom Brachytherapy Carriers."

Tile Carrier (also referred to as "Tile"): type of carrier that is substantially planar and generally maintains a two-dimensional planar geometry when placed in a tumor bed. Depending on the material of the tile, though, the tile may be malleable such that the tile can be deformed by bending in order to better conform to a tumor bed. For example, for tiles comprising essentially collagen (and/or other malleable materials), the tiles may be substantially bent as placed in or on a treatment surface (and/or when pressed against the treatment surface) to conform with the shape of the treatment surface, such as a post-operative tumor bed.

Custom Carrier: a carrier having one or more non-planar surfaces, such as a spherical shape or having a spherical portion. Examples of custom carriers include Spherical Carriers, Gore Carriers, and Star Carriers, noted below, as well as other custom carriers discussed herein. A custom carrier may be non-symmetrical in any dimension and/or configured to conform to any given shape (e.g., cavity configuration).

Spherical Carrier (or "GammaSphere"): a substantially radially symmetrical body around an axis. A spherical carrier may also include a non-spherical portion, such as a tapered portion that extends from a spherical portion. Examples of other variations of spherical carriers are discussed in U.S. Patent Application No. 63/163,583, filed Mar. 19, 2021, entitled "Custom Brachytherapy Carriers," which is incorporated by reference in its entirety and for all purposes.

Gore Carrier (also referred to as "Gore"): type of carrier that is 3-dimensional and conforms to the tumor bed while maintaining the geometry necessary for an effective implant. In some embodiments, gores are initially planar and are reconfigured to take on a 3-dimensional shape, such as to form a hemispherical surface that may be placed into a similarly shaped tumor cavity. Gore Carriers are further discussed in U.S. Pat. No. 8,876,684, entitled "Dosimetrically customizable brachytherapy carriers and methods thereof in the treatment of tumors," filed on Jul. 2, 2014 as application Ser. No. 14/322,785, which is hereby incorporated by reference in its entirety and for all purposes.

Star Carrier (also referred to as "Star" or "arm-based carrier"): type of carrier that assumes a conformable 3-dimensional shape when arranged and placed into an operative cavity or similar space and conforms to the treatment environment while maintaining the geometry necessary for an effective implant. However, in some embodiments, Star carriers may be used in their initial planar state to cover a relatively flat tumor or tumor bed area. Star carriers are further discussed in U.S. Pat. No. 9,492,683, entitled "Dosimetrically customizable brachytherapy carriers and methods thereof in the treatment of tumors," filed on Mar. 17, 2014 as application Ser. No. 14/216,723, which is hereby incorporated by reference in its entirety and for all purposes.

Loader: a device that aids in placement of radioactive seeds in carriers, such as via injection of seeds into carriers. A loader, also referred to herein as a "loading device," may include multiple components, such as to hold a carrier in place and guide a delivery device (e.g., a needle or injector) into the carrier in order to place a seed at a precise location in the carrier. The "Loader Patents" refers to U.S. patent application Ser. No. 13/460,809, filed Apr. 30, 2012, now U.S. Pat. No. 8,939,881, entitled "Apparatus For Loading Dosimetrically Customizable Brachytherapy Carriers," and U.S. patent application Ser. No. 14/696,293, filed Apr. 24, 2015, entitled "Apparatus and Method for Loading Radioactive Seeds Into Carriers," which are each hereby incorporated by reference in their entirety for all purposes, describe several embodiments of loaders. As discussed further herein, loaders may be operated manually, such as by human operators, or may be fully automated, such that carriers can be loaded with seeds using an automated process. Alternatively, loaders may be configured to be automated in part and require manual operation in part.

Shielding Material: any material that restricts movement of radioactive particles, such as by absorbing, reflecting, and/or scattering radioactive particles. The term "shielding," as used herein, generally refers to any mechanism of preventing radiation from moving through and exiting a corresponding shielding material, such as by the shielding material absorbing, reflecting, or otherwise blocking the radiation. Shielding materials in various forms may be used in the various embodiments discussed herein. For example, a shielding material may be in the form of a particle, wire, rod, cylinder, bar, sheet, liquid, solution, foam, or any other form in which a material having radiation absorbing and/or reflecting properties is possible. A shielding material provides a shielding rate, which is generally an amount of shielding of radioactive energy (that is emitted from one or more radiation sources), provided by the particular shielding materials. Similarly, a shielding layer comprising multiple shielding materials and an isolation sheet have associated shielding rates, which are dependent on the combination of shielding (and possibly non-shielding) materials therein. For some applications, such as based on clinical need, an isolation sheet that provides a shielding rate of 25%, 50%, 75%, 90%, 95%, 98%, or some other shielding percentage, may be desired. As discussed herein, material composition, shape, size, dimensions, etc. may impact the shielding abilities of a shielding material. For applications (e.g., based on clinical need) where a higher shielding percentage is desired than may be provided by a single shielding material, multiple shielding materials may be used in combination, in one or more shielding layers or isolation sheets.

High Z Materials: any element with an atomic number greater than 20, or an alloy containing such materials.

Hot Carrier: a carrier that is loaded with a material that is radioactive.

Cold Carrier: a carrier that is not loaded a material that is radioactive, such as a carrier prior to loading of a radioactive seed.

Dosimetry: a process of measurement and quantitative description of the radiation absorbed dose (rad) in a tissue or organ.

Treatment Specifications: any information that is useful in selecting and/or manufacturing of custom radioactive seed carriers for a particular patient, such as based on a treatment plan developed for the patient. Treatment specifications may include information regarding a tumor cavity into which the custom carriers will be used, such as cavity size, cavity shape, etc. Treatment specifications may also include a desired dose of radiation to be realized to a treatment surface of the patient. In some implementations, treatment specifications may include further details, such as an indication of preferred sizes, shapes, materials, etc. of carriers.

Example Custom Carrier System

FIG. 1 is a high-level diagram of a system of devices usable to create custom carriers for use in brachytherapy. In the embodiment of FIG. 1, a treatment planning system 110 determines a brachytherapy treatment plan for a particular patient, or other mammal. The treatment plan may indicate, for example, a radiation dosage that a radiation oncologist has prescribed for administration to a treatment surface of a tumor cavity that remains after removal of a tumor from a patient. The treatment planning system 110 provides treatment specifications 115 to a custom carrier system 120. The treatment specifications 115 may include, for example information regarding a shape and size of the treatment cavity and/or the treatment surface (e.g., the surface of the cavity to receive radioactive carriers), as well as a desired radiation dose to be provided. The radiation dose may include multiple dosage indications for different areas of the treatment surface, such as to indicate a higher dosage at a portion of the treatment surface closest to the removed tumor and a lower dosage at a portion of the treatment surface further from the removed tumor.

In the example of FIG. 1, custom carrier system 120 includes a carrier specification component 121 configured to receive and process the treatment specifications 115 to determine specifications for one or more custom carriers that satisfy the treatment specifications 115. The carrier specification component 121 may include software configured to automatically determine a best fit of carriers (e.g., carrier sizes, shapes, materials, seed quantity, seed strength, etc.) that satisfy the treatment specifications 115, which is generally referred to herein as the custom carrier configuration or carrier configuration. In some embodiments, best fit parameters that are used to guide development of the carrier configuration may be defined by the software provider, by the treatment planner, and/or by the surgeon that will be performing the brachytherapy procedure. Such best fit parameters may include preferences for lower or higher quantity of carriers, smaller or larger sizes of carriers, ranges of radioactive dosages, strength of radioactive seeds, quantity of radioactive seeds, position or orientation of radioactive seeds, material preferences for the custom carriers, and/or any other parameter. In some embodiments, similar parameters may be included in the treatment specifications 115.

In some embodiments, the treatment specifications 115 may be automatically analyzed by the carrier specification component 121 to determine the carrier configuration, such as indicating a quantity of carriers, shapes and sizes of those carriers, quantity of radioactive seeds for each carrier, position of radioactive seeds in each carrier, and the like. Thus, the carrier specification component 121 allows a treatment planner, such as a radiation oncologist using the treatment planning system 110, to simply provide the desired treatment specifications, while leaving generation of the custom carrier configuration to the custom carrier system. In some embodiments, the treatment planner (e.g., and the treatment planning software used on the treatment planning system 110) may be configured to allow selection of the carrier configuration for a particular treatment plan. Thus, in such an embodiment the carrier configuration may be included as part of the treatment specifications 115, or in place of the treatment specifications 115.

Once the carrier specification component 121 has determined the carrier configuration, a custom carrier component 122 creates the custom carriers. Depending on the embodiment, the custom carrier component 122 may include various carrier manufacturing hardware, software, and materials. For example, the carrier specification component 121 may automatically transmit instructions to the custom carrier component 122, which may then in turn automatically create custom carriers based on the received custom carrier configuration.

Figure 2:
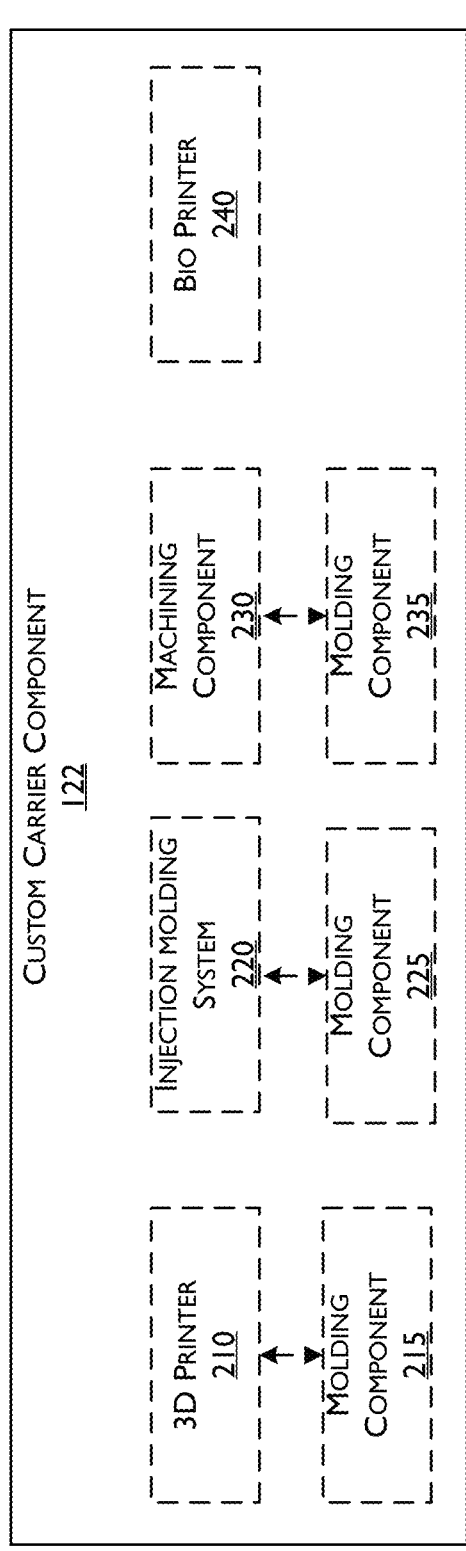
FIG. 2 illustrates example devices and methods for creating a custom carrier.

FIG. 2 illustrates some example devices and methods that may be utilized by the custom carrier component 122 in creation of custom carriers. Each of the 3D printer 210, injection molding system 220, and machining component 230 are configured to first manufacture a custom mold, which is then usable to create the custom carriers using the mold.

For example, 3D printer 210 may receive some or all of the carrier configuration indicating specific printing details one or more carrier molds. The printing details may include Computer-Aided Design (CAD) information describing the mold (or molds), such as in a known file type, e.g., a stereolithography file format (STL). The printing details may further include an indication of material, such as plastic, metal, or other suitable material. In some implementations, the custom carrier component 122 as access to multiple 3D printers, and selects one of the 3D printers for a new print job based on the printing details.

Figure 7A:
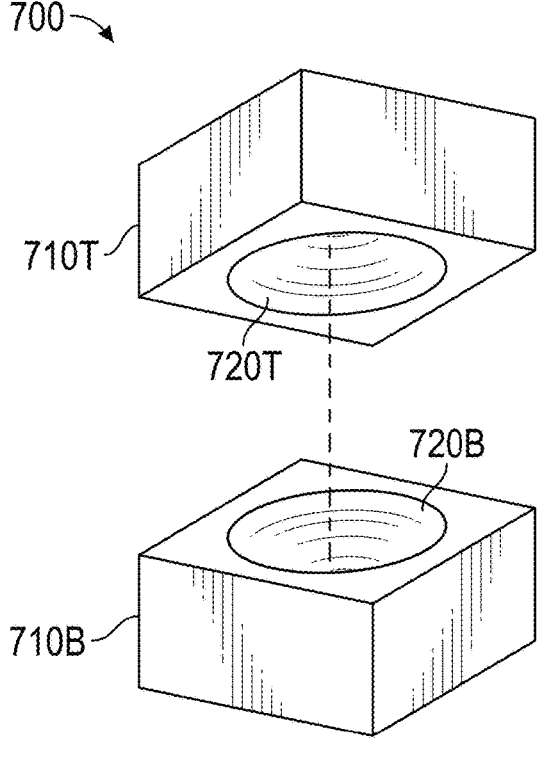
FIGS. 7A and 7B are perspective and side views of a custom carrier mold including a top and bottom portion.
Figure 7B:
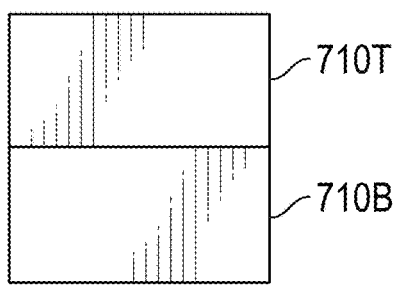
Figure 7C:
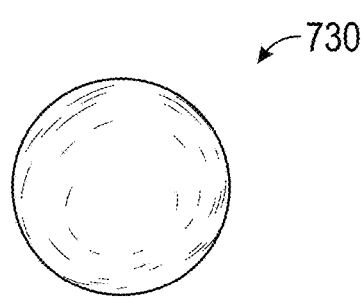
FIG. 7C is a perspective view of a custom carrier created with the mold of FIGS. 7A and 7B.

As one example, a carrier mold may include a bottom and a top portion, each with one or more cavities sized such that when a bioresorbable material is placed in the cavities and the top and bottom portions are joined together, a carrier with dimensions specified in the carrier configuration is produced. For example, FIGS. 7A and 7B illustrate a custom mold 700 configured to mold the custom carrier 730 of FIG. 7C. In an embodiment where the custom carrier component 122 comprises a 3D printer 210, a top portion 710T and a bottom portion 710B of the custom mold 700 may be printed by the 3D printer, either in a concurrent print or sequentially one after the other. As shown in FIG. 7A, the top portion 710T includes a hemispherical cavity 720T, while the bottom portion 710B includes a similar hemispherical cavity 720B. Advantageously, when the top portion 710T and the bottom portion 710B of the custom mold 700 are aligned and placed together, such as in the side view of FIG. 7B, the cavities 720T and 720B form a spherical cavity. Thus, a bioresorbable material, such as collagen or a derivative thereof, may be placed within the cavities to form a spherical carrier 730. With reference to FIG. 2, the molding component 215 may comprise an automated and/or manual device that introduces the carrier material into the cavity 720, closes the mold for drying, curing, and/or hardening of the carrier material within the cavity (e.g., as in FIG. 7B), and/or opens and removes the molded custom carrier 730 from within the cavity 720.

Injection molding system 220 may be used in a similar manner as 3D printer 210. For example, an injection molding system 220 may create molds similar to those shown in FIG. 7A via an injection molding process. Thus, the molding component 225 may perform in a similar manner as molding component 215 to create a custom carrier using a mold manufactured using the injection molding system 220.

Machining component 230 may be used in a similar manner as 3D printer 210 and/or injection molding system 220. For example, a machining component 230 may mill, drill, cut, reem, etc. a void into a substrate material to form cavities that are usable to create a custom carrier. For example, a machining component 230 may remove portions of a planar substrate (e.g., metal, wood, plastic, etc.) to create a hemispherical cavity in the substrate, such as mold portions 710T and 710B of FIG. 7A. A molding component 235 may perform in a similar manner as molding components 215 and 225 to then use the machined mold in production of one or more carriers.

In some embodiments, any of the molding components 210, 220, 230, may generate a single structure mold, such as a cubicle structure with an internal spherical cavity. In such an embodiment, one or more injection channels extending from an outer surface of the mold to the cavity may be included in the mold, so that a viscous carrier material may be injected into the spherical cavity.

A printer bioprinter 240 may also be used to generate custom carriers based on the carrier configuration developed by the carrier specification component 121. The bioprinter 240 may, for example, print layers of a bioink (e.g., liquefied collagen or similar bioresorbable material) in the shape of the custom carrier, without the need for a mold. For example, the carrier 730 of FIG. 7C may be bioprinted according to the carrier configuration, such as with supports printed on the lower portions of the spherical carrier that may be removed once printing is complete. In some embodiments, a bioprinter 240 may be configured to insert a radioactive seed into a partially printed carrier, such as when the carrier is about half printed so that the radioactive seed is centrally located within the carrier when the top half of the carrier is fully printed. In some embodiments, the bioprinter 240 may work in conjunction with a seed insertion device that inserts the radioactive seed at the appropriate time onto the partially printed carrier, such as in response to a signal from the bioprinter 240.

Returning to FIG. 1, a lyophilization component 124 optionally lyophilizes the custom carriers. A lyophilization process generally performs a process of freeze-drying the custom carriers. In some embodiments, lyophilization of the custom carriers may not be performed.

Next, a seed loading component 126 loads the custom carriers with radioactive seeds as indicated in the carrier configuration, such that loaded carriers collectively provide a best fit of the treatment specifications 115. The seed loading component 126 may include automated and/or manual seed loading processes, such as using various combinations of loading devices and techniques, including those described in the Loader Patents.

With the radioactive seeds loaded into the carriers, a sterilization component 128 optionally serializes the loaded (or "hot") carriers. The hot carriers are then transported to a surgery center 130 where they will be implanted into the tumor cavity of the patient.

Figure 3:
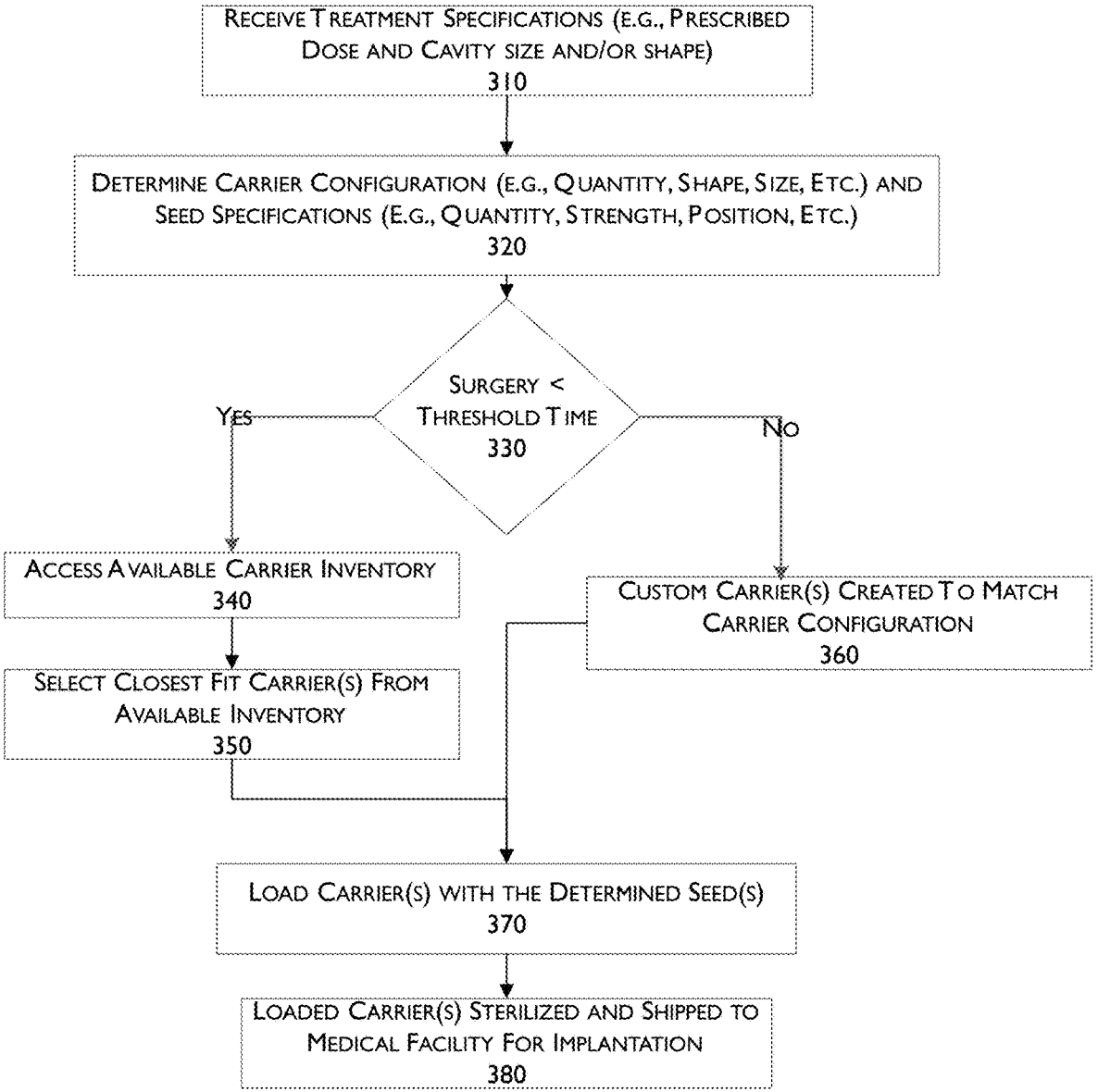
FIG. 3 is a flowchart illustrating one example of a method of manufacturing custom carriers that may be performed prior to a scheduled brachytherapy process for the patient.

FIG. 3 is a flowchart illustrating one example of a method of manufacturing custom carriers that may be performed prior to a scheduled brachytherapy process for the patient. In one embodiment, the process of FIG. 3 may be performed by the custom carrier system 120, which may be remote to the treatment planning system 110 and/or the surgery center 130. In other embodiments, portions of the process may be performed by the treatment planning system 110 and/or the surgery center 130. Depending on the embodiment, the method of FIG. 3 may include fewer or additional blocks and the blocks may be performed in an order that is different than illustrated.

Beginning at block 310, treatment specifications are received, such as from a treatment planning system 110. As noted above, the treatment specifications may include a prescribed dose, as well as cavity specifications, such as size and/or shape of the cavity into which the custom carriers will be placed. In other embodiments, the treatment specifications may include different or additional information.

Moving to block 320, configuration of one or more carriers is determined based on the treatment specifications. For example, a carrier configuration may indicate configuration of each of one or more carriers that has been determined by the custom carrier component 122 (FIG. 1) to meet the treatment specifications for the particular patient. A carrier configuration may include a quantity, shape, size, etc. of one or more carriers, as well as radioactive seed specifications, such as quantity, strength, position, etc. of radioactive seeds that will be inserted into the custom carriers. For example, the carrier configuration may indicate for each of multiple carriers, a shape and size of the carrier (which may include multiple shapes and sizes of carriers) as well as a quantity, strength, and position of radioactive seeds for each of the carriers (which may vary from one carrier to another). In some embodiments, a carrier configuration includes a user readable visualization (e.g., a printed document that may be sent with the custom carriers and/or an electronic user interface, such as a webpage or PDF, that is accessible by the surgery center) indicating the proper location and orientation of each of the carriers in the tumor cavity according to the carrier configuration.

Next, at block 330, a determination is made whether the surgery where implantation of the custom carriers will be performed is less than a threshold time period away. The threshold time period may be the time that is needed to reliably manufacture custom carriers according to the determined carrier configuration and transport the custom carriers to the corresponding surgery center. In some embodiments, the custom carrier manufacturing requires a predetermined minimum time, such as six hours, twelve hours, one day, two days, three days, etc. In some embodiments, the manufacturing time depends on other factors, such as the number of custom carriers, number of custom carrier molds, radiation dosage, availability of materials for implementation of the carrier configuration, and/or any other factors that may affect time required for manufacturing custom carriers. Additionally, transport of custom carriers to the surgery center may be a fixed time period, or may vary depending on distance from the custom carrier manufacturing facility in the surgery center, for example. Thus, the threshold time may vary depending on multiple factors.

If a scheduled surgery is before an expected delivery of the custom carriers to the surgery center (e.g., a current day and time plus a threshold time required for manufacture and delivery of the custom carriers), an alternate process may be performed wherein current carrier inventory is accessed to expedite provision of carriers at the surgery center. For example, at block 340, the system automatically and/or manually accesses available carrier inventory, which may include various sizes, shapes, materials of carriers that are stored at the custom carrier manufacturing facility and/or other carrier storage facilities. Thus, the system may access inventory at multiple facilities, including facilities that may be closer to the surgery center than the custom carrier system 120 and, thus, may require less time for transport of carriers to the surgery center.

Next, at block 350, the system determines the closest fit of carriers from the available inventory to the determined carrier configuration. Because custom carriers may not be generated in time for the surgery (as determined at block 330), carriers that do not exactly meet the carrier configuration determined at block 320 may be analyzed in various combinations to identify an alternate carrier configuration that still satisfactorily provides the treatment specifications.

Alternatively, if at block 330 the system determines that there is sufficient time to generate custom carriers according to the determined carrier configuration, the method moves to block 360 where one or more custom carriers are created to match the carrier configuration. In some embodiments, this custom carrier manufacturing process, such as is discussed in FIG. 1, uses one or more custom carrier components 122, such as those illustrated in FIG. 2.

With either custom carriers manufactured at block 360 or standard carriers selected from inventory at block 350, the method continues to block 370 where the carriers are loaded with the radioactive seeds determined by the carrier configuration or the alternate carrier configuration if standard carriers are used. As noted above, loading of seeds may be performed by various methods, such as those discussed in the Loader Patent.

Next, at block 380 the loaded carriers are optionally sterilized and shipped to the medical facility for implantation. Depending on the embodiment, transportation of the loaded carriers may be performed by a custom carrier (e.g., UPS, FedEx, USPS, etc.) or may be a specialized charter delivery service that customizes in delivery of medical devices and/or radioactive materials.

FIG. 4 is a flowchart illustrating one embodiment of an intra-operative process for generating custom loaded carriers. For example, the process of FIG. 4 may be performed while the patient is undergoing a tumor removal surgery, such as in the operating room and/or adjacent facilities of the surgical center. Thus, the process of FIG. 4 allows expedited selection and use of custom carriers. Depending on the embodiment, the method of FIG. 4 may include fewer or additional blocks and the blocks may be performed in an order that is different than illustrated.

Beginning at block 410, treatment specifications for the patient are received and/or determined by a surgeon, oncologist, and/or others at (or in contact with) the surgical facility. For example, in some implementations the treatment specifications are determined in real-time as the tumor is removed and/or shortly after the tumor is removed, so that the custom carriers may be implanted during the same surgical procedure.

At block 420, custom carrier configuration is determined, such as in a similar manner as block 320 discussed above. In some embodiments, the custom carrier configuration at block 420 may be limited to provide a carrier configuration that is possible with the custom carrier components 122 that are available during the intraoperative process.

Next, at block 430, available carrier inventory is accessed to determine standard carriers that are available for use in the current surgical procedure. For example, carriers that are located at the surgical facility may be included in the available standard carrier inventory, as well as other carriers that are within a close proximity to the surgical facility such that they could be delivered to the surgical facility within a threshold time period (e.g., 20 minutes, 40 minutes, 60 minutes, two hours, etc.) that may be set to a default time period and/or customized by the surgical team.

Moving to block 440, a closest fit of carriers and/or radioactive seeds from the determined available inventory that achieves the determined carrier configuration and treatment specifications are selected. Then, at block 450, a determination is made whether the closest fit is satisfactory for the surgical team to proceed with implantation. In some embodiments, summary information regarding the determined closest fit is provided to the surgical team for evaluation and determination of whether the closest fit meets the treatment specifications. In some embodiments, the system may automatically determine whether the closest fit is satisfactory at block 450, such as based on threshold allowable differences in various parameters of the treatment specifications.

If at block 450 a determination is made that the closest fit is not satisfactory, one or more custom carriers may be created aseptically, such as bioprinted at the surgical facility itself, to match the carrier configuration. For example, the processes discussed above with reference to bioprinter 240 may be performed at the surgical facility. Alternatively, other carrier components may be used to generate custom carriers, such as a machining process that machines a custom mold usable immediately for manufacture of custom carriers matching the carrier configuration.

If at block 450 a determination is made that the closest fit is satisfactory, the method continues to block 470, where the existing carriers from inventory are loaded with the best fit radioactive seeds from inventory to meet the closest fit of the carrier configuration and/or other treatment specifications, such as seed strength, seed quantity, and the like. Alternatively, if custom carriers were created at block 460, those custom carriers are loaded at block 470 with the determined seeds to match the carrier configuration. In either case, the loaded carriers are available for immediate implantation at block 480.

Figure 5A:
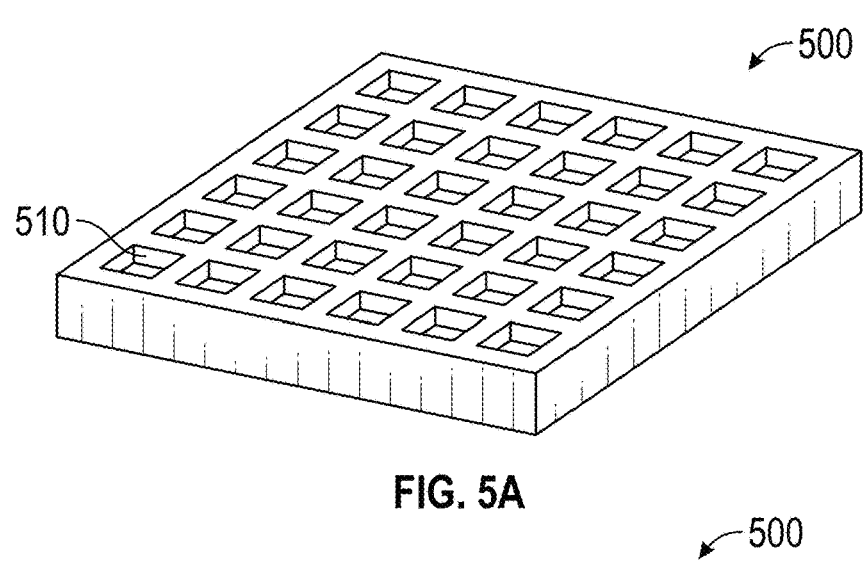
FIGS. 5A and 5B are perspective and top views of a custom carrier mold for generation of an array of cube shaped carriers.
Figure 5B:
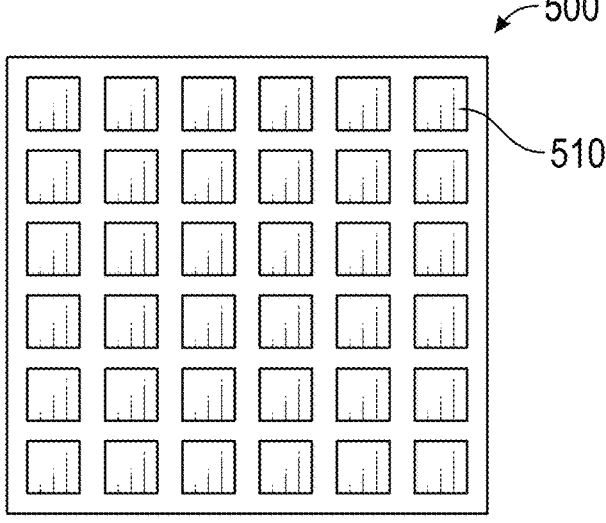
Figure 5C:
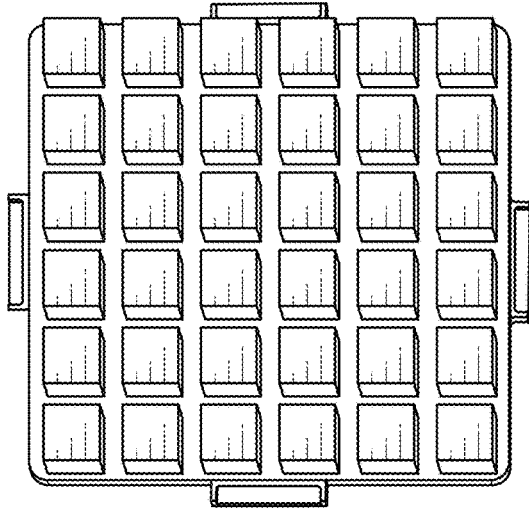
FIG. 5C is an example of a series of custom carriers that may be generated using the example mold of FIGS. 5A and 5B.

FIG. 5A is a perspective view and FIG. 5B is a top view of a custom carrier mold 500 for generation of an array of thirty-six cube shaped carriers. The mold 500 may be generated by any of the custom carrier components 210, 220, 230. The example custom carrier mold 500 includes thirty-six cavities 510 configured to receive and to shape a bioresorbable material into a cube shaped carrier. In some embodiments, the bioresorbable material is placed into the cavities 510 and allowed to dry, cure, and/or harden, as applicable. After drying or curing, if applicable, the carriers may be extracted from the cavities 510, such as by inverting the carrier mold 500 to cause the custom carriers to fall out of the mold 500. In some embodiments, a top mold (not shown) that substantially mirrors the mold 500 with thirty-six cavities may be attached to the mold 500 as part of the molding process. FIG. 5C is an example of a series of custom carriers that may be generated using the example mold of FIGS. 5A and 5B.

Figures 6A, 6B:
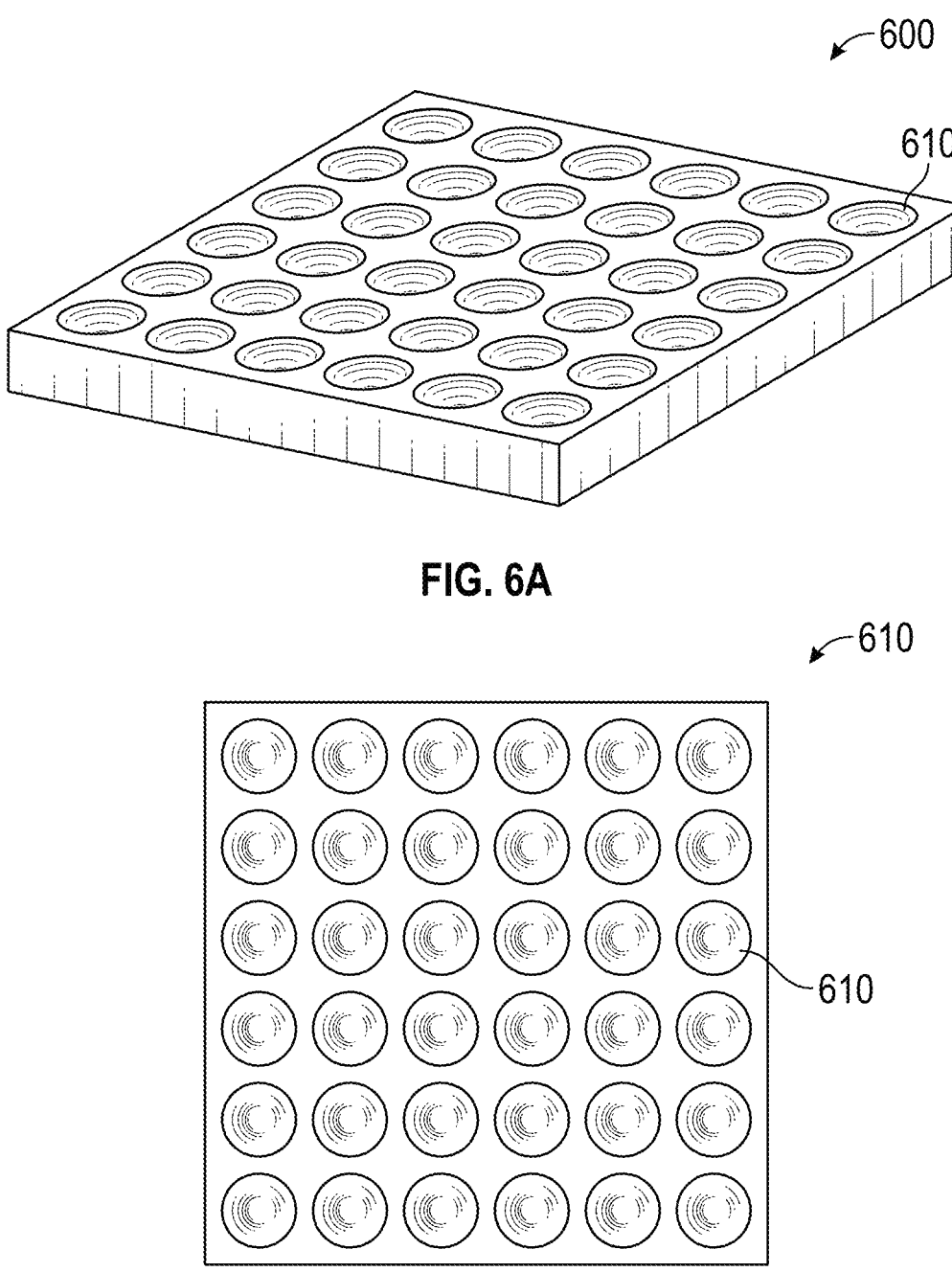
FIGS. 6A and 6B are perspective and top views of another custom carrier mold for generation of an array of hemispherical carriers.

FIG. 6A is a perspective view and FIG. 6B is a top view of another custom carrier mold 600 for generation of an array of thirty-six hemispherical carriers. The mold 600 may be generated by any of the custom carrier components 210, 220, 230. As shown, the mold 600 includes hemispherical cavities 610 configured to receive and shape a bioresorbable carrier material into a hemispherical carrier. In some embodiments, each of the carriers manufactured with the hemispherical mold 600 may be adhered to in other hemispherical carrier to form a spherical carrier. Additionally, a radioactive seed may be placed in a central portion of a first hemispherical carrier prior to attachment of a second hemispherical carrier, thereby embedding the radioactive seed into a central portion of the resultant spherical carrier. A similar seed embedding technique may be used with other shapes of carriers, such as the cube shaped carriers of FIG. 5. In other embodiments, a top mold (not shown) that substantially mirrors the mold 600 may be attached to the mold 600 to allow molding of full spherical carriers.

As discussed above, FIGS. 7A and 7B illustrate a custom carrier mold 700 including a top and bottom portion. The mold 700 may be generated by any of the custom carrier components 210, 220, 230, e.g., as part of a custom carrier manufacturing process. Depending on the embodiment, a custom carrier mold configured for molding of any quantity of custom carriers (e.g., from one custom carrier as shown in the embodiment of FIG. 7A to thirty-six custom carriers in the embodiments of FIGS. 5 and 6, or even more) may be created and used for custom carrier molding.

FIG. 8A illustrates another custom mold 800 that is configured to produce a spherical fluted carrier 830 (FIGS. 8B and 8C). The mold 800 may be generated by any of the custom carrier components 210, 220, 230, e.g., as part of a custom carrier manufacturing process. In this example, the custom mold 800 includes a top portion 810T configured for attachment to a bottom portion 810B to produce a carrier having the shape of the combined cavities 820T and 820B. As explained in U.S. Patent Application No. 63/163,583, filed Mar. 19, 2021, entitled "Custom Brachytherapy Carriers," which is hereby incorporation by reference in its entirety and for all purposes, fluting of carriers may provide various advantages, such as an ability for fluid (e.g., air or liquid) delivery and/or drainage to/from a cavity via the flutes on the exterior of the carriers. In other embodiments, any other shape or size of carrier may be generated using the custom carrier processes discussed herein.

Figure 9A:
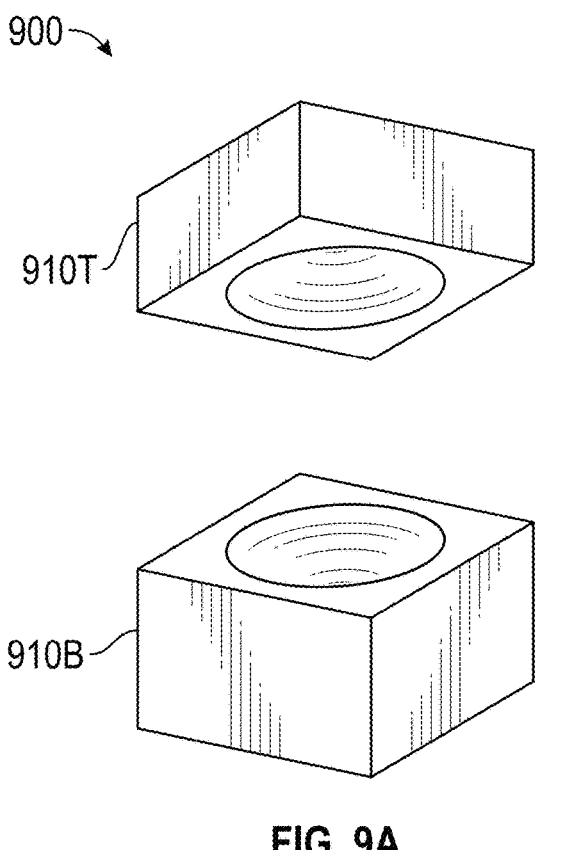
FIGS. 9A and 9B are perspective and side views of another custom carrier mold.
Figure 9B:
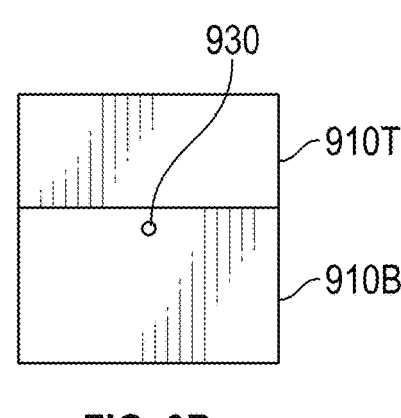

FIGS. 9A and 9B illustrate another custom carrier mold 900, which may be generated by any of the custom carrier components 210, 220, 230, e.g., as part of a custom carrier manufacturing process. The example mold 900 includes a top portion 910T having a height that is less than the height of a bottom portion 910B. For example, in one embodiment the bottom portion 910B may comprise 60% of the total height of the combined mold 900 (e.g., 0.60 cm of a 1 cm mold height) while the top portion 910T comprises 40% of the total height of the combined mold (e.g., 0.40 cm of a 1 cm mold height). In this embodiment, a seed insertion channel 930 is included in the mold, and positioned at a central height of the resultant spherical carrier. In this embodiment, the mold 900 serves as a seed loading device also, which may be accomplished through introduction of a seed introduction device (e.g., a needle, pushrods, etc.) into the channel 930, and further into the bioresorbable material of the carrier formed within the mold 900. In some embodiments, the mold 900 with loaded (e.g., "hot") carrier within the mold may also serve as a shipping container for the carrier, which may be transported to the surgical center where the hot carrier is removed from the mold 900.

Figure 9C:
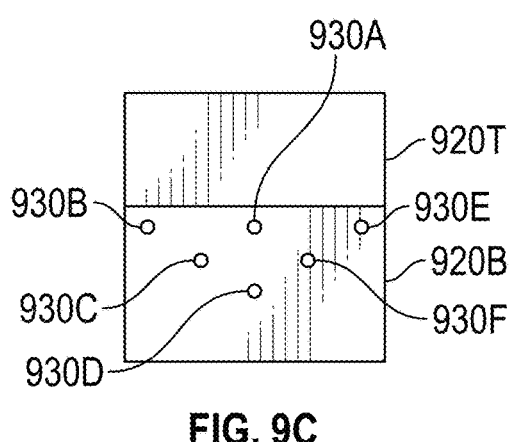
FIG. 9C is a side view of another example custom carrier mold.

FIG. 9C is another example custom carrier mold having a top portion 910T and bottom portion 910B. In this embodiment, the custom carrier includes multiple seed insertion channels 930A-930F configured to guide an insertion device (e.g., a needle or pushrod) into a specific portion of the custom carrier for embedding of one or more radioactive seeds. For example, a spherical carrier fabricated in the custom carrier mold of FIG. 9C may be loaded with radioactive seeds at peripheral locations (via seed insertion channels 930B-F and/or at a central location (via seed insertion channel 930A). In some embodiments, the top portion 910T may have similar seed insertion channels positioned for seed insertion at the upper periphery of a custom carrier.

In any of the embodiments discussed herein, the custom carrier molds may be configured to allow markings to a custom carrier. For example, an inner surface of the top portion 910T may be textured (e.g., uneven, such as ribbed) while an inner surface of the bottom portion 910B is not textured (e.g., is smooth). Thus, a top of any spherical carriers fabricated with this example custom carrier mold will include tactile markings (which may also be visually identifiable) to differentiate from the bottom of the spherical carrier once removed from the mold.

In some embodiments, markings may be added to custom carriers, such as carriers 730 or 830, after fabrication. For example, one or more visual markings may be applied to a custom carrier via pad-printing on the carrier surface, such as to denote seed position, orientation, strength, shielding (e.g., wrapped seed shielding), and/or other characteristics of the custom carrier.

Markings, which may be visual and/or tactile, may indicate a proximal portion of the custom carrier that should contact (or be closest to) the treatment surface. Alternatively, markings may indicate a distal portion of the custom carrier that should be furthest away from the treatment surface. Markings may also include cut or trim lines indicating where a custom carrier can be cut, such as between locations of radioactive seeds. In some implementations, markings may indicate location of each radioactive seed embedded in a custom carrier and/or a strength of each of the radioactive seeds, such as using a color coding scheme or printing the numerical radiation strength (e.g., in Gy) on the surface of the custom carrier. Similarly, markings may indicate location of shielding, such as to indicate a distal portion of the carrier.

Other Embodiments

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, the use of particular terminology when describing certain features or aspects of the invention should not be taken to imply that the terminology is being redefined herein to be restricted to including any specific characteristics of the features or aspects of the invention with which that terminology is associated. The scope of the invention should therefore be construed in accordance with the appended claims and any equivalents thereof.

What is claimed is:

1. A method comprising:
receiving treatment specifications including at least a tumor cavity size and shape and a radiation dose;
determining a carrier configuration based on the treatment specifications, the carrier configuration indicating, for at least a first custom carrier, a carrier shape and a radioactive seed quantity;
based at least on the carrier configuration, generating the first custom carrier using one or more custom carrier components, the one or more custom carrier components including one or more of a 3D printer, injection molding system, machining component, or bioprinter;
based at least on the radioactive seed quantity indicated in the carrier configuration, inserting one or more radioactive seeds into the first custom carrier according to a seed position indicated in the treatment specifications; and
providing the first custom carrier for implantation into a cavity of a particular mammal.

2. The method of claim 1, wherein the carrier configuration further includes radioactive seed strength and radioactive seed orientation.

3. The method of claim 1, wherein the first custom carrier has a thickness between one and seven centimeters.

4. A method comprising:
receiving treatment specifications including at least a tumor cavity size and shape and a radiation dose;
determining a carrier configuration based on the treatment specifications, the carrier configuration indicating, for at least a first custom carrier, a carrier shape and a radioactive seed quantity;
based at least on the carrier configuration, determining a custom mold configuration;
providing the custom mold configuration to a 3D printer;
forming the first custom carrier using a custom mold created by the 3D printer;
based at least on the radioactive seed quantity indicated in the carrier configuration, inserting one or more radioactive seeds into the first custom carrier;
lyophilizing the first custom carrier;
sterilizing the first custom carrier; and
initiating transport of the first custom carrier to an implantation location, wherein the first custom carrier is specially designed for implantation into a cavity of a particular mammal.

5. The method of claim 4, wherein the first custom carrier is rectangular.

6. The method of claim 4, wherein the first custom carrier is spherical.

7. The method of claim 6, wherein the first custom carrier has a diameter between one and seven centimeters.

8. The method of claim 4, wherein the first custom carrier is shaped and sized to correspond to the tumor cavity.

9. The method of claim 4, wherein the first custom carrier is configured for separation into a plurality of smaller custom carriers for implantation into the cavity of the particular mammal.

10. The method of claim 9, wherein said separation is performed with a cutting device.

11. The method of claim 9, wherein the first custom carrier includes one or more markings indicating locations where the first custom carrier is configured for separation.

12. The method of claim 4, wherein said lyophilizing the first custom carrier reduces an area of the first custom carrier by more than twenty percent.

13. The method of claim 12, wherein the first custom carrier is configured to expand upon hydration.

14. The method of claim 13, wherein said hydration is provided by saline or a bodily fluid.

15. The method of claim 4, wherein the carrier configuration further includes radioactive seed strength and radioactive seed orientation.

16. A method comprising:
receiving treatment specifications including at least a tumor cavity size and shape and a radiation dose;
determining a desired carrier configuration based on the treatment specifications, the desired carrier configuration indicating, for at least a first custom carrier, a carrier shape and a radioactive seed quantity;
determining a closest fit carrier already fabricated and available for implantation, the closest fit carrier having an available carrier configuration, and:
  in response to determining, based on a comparison of that the available carrier configuration with the desired carrier configuration, that the closest fit carrier is not satisfactory, generating the first custom carrier using one or more custom carrier components, the one or more custom carrier components including one or more of a 3D printer, injection molding system, machining component, or bio-printer; or
  in response to determining, based on a comparison of that the available carrier configuration with the desired carrier configuration, that the closest fit carrier is satisfactory, initiating retrieval of the closest fit carrier without generating the first custom carrier.

17. The method of claim 16, further comprising:
selecting a plurality of radioactive seeds having seed strengths indicated in the treatment specifications; and

implanting the plurality of radioactive seeds at positions and orientations indicated in the treatment specifications.

18. A method comprising:
receiving treatment specifications including at least a tumor cavity size and shape and a radiation dose;
determining a desired carrier configuration based on the treatment specifications, the desired carrier configuration indicating, for a custom carrier, a carrier shape and a radioactive seed quantity;
determining whether a surgery where implantation of the custom carrier will be performed is less than a threshold time period away, and:
  in response to determining that the surgery is less than a threshold time period away, determining a closest fit carrier already fabricated and available for implantation, the closest fit carrier having an available carrier configuration closest to the desired carrier configuration, and initiating retrieval of the closest fit carrier; or
  in response to determining that the surgery is not less than a threshold time period away, initiating generation of the custom carrier having the desired carrier configuration using one or more custom carrier components, the one or more custom carrier components including one or more of a 3D printer, injection molding system, machining component, or bio-printer.

19. The method of claim 18, further comprising:
sterilizing the custom carrier prior to implantation.

20. The method of claim 18, further comprising:
selecting a plurality of radioactive seeds having seed strengths indicated in the treatment specifications; and
implanting the plurality of radioactive seeds at positions and orientations indicated in the treatment specifications.

* * * * *